US00PP23389P2

(12) United States Plant Patent
Korlipara

(10) Patent No.: US PP23,389 P2
(45) Date of Patent: Feb. 12, 2013

(54) ***GAILLARDIA* PLANT NAMED 'RED SUN'**

(50) Latin Name: *Gaillardia×grandiflora*
Varietal Denomination: Red Sun

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 4 days.

(21) Appl. No.: 13/200,422

(22) Filed: Sep. 23, 2011

(51) Int. Cl.
*A01H 5/00* (2006.01)

(52) U.S. Cl. ..... Plt./431

(58) Field of Classification Search ..... Plt./431
See application file for complete search history.

*Primary Examiner* — Susan McCormick Ewoldt
(74) *Attorney, Agent, or Firm* — Klarquist Sparkman, LLP

(57) ABSTRACT

A new and distinct *Gaillardia* plant named 'Red Sun' characterized by a very compact habit, ray florets of dark red tipped with orange, overlapping ray florets in multiple layers, and excellent vigor.

1 Drawing Sheet

Botanical denomination: *Gaillardia×grandiflora.*
Variety designation: 'Red Sun'.

BACKGROUND OF THE INVENTION

The present invention relates to a new and distinct cultivar of *Gaillardia×grandiflora* and given the cultivar name 'Red Sun'. *Gaillardia* is in the family Asteraceae. This new cultivar is a third generation seeding originating from a planned breeding program to create new dwarf *Gaillardia*. The exact parents are unknown, unreleased, proprietary plants.

Compared to *Gaillardia* 'Sunburst Burgundy' (unpatented), the new cultivar is more compact and has orange tips on the red ray florets.

Compared to *Gaillardia* 'Arizona Sun' (unpatented), the new cultivar has darker flowers with orange only on the tips and more ray florets.

SUMMARY OF THE INVENTION

This new *Gaillardia* cultivar is distinguished by:
1. a very compact habit,
2. ray florets of dark red tipped with orange,
3. overlapping ray florets in multiple layers, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows *Gaillardia* 'Red Sun' in full bloom as a 6 month old in the field in full sun in early August in Canby, Oreg.

DETAILED PLANT DESCRIPTION

The following is a detailed description of the new *Gaillardia* cultivar based on observations of 6-month-old specimens growing in the ground in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:
- *Type.*—Herbaceous perennial.
- *Hardiness.*—USDA Zones 3 to 9.
- *Size.*—Grows to 42 cm wide and 38 cm tall to top of inflorescences.
- *Form.*—Basal clump, with about 6 main stems from the base.
- *Vigor.*—Excellent.
- *Roots.*—Fibrous, with many downward growing and few laterals, ivory in color, Yellow White 158D, roots develop easily from stem cuttings.

Stem:
- *Type.*—Ascending.
- *Size.*—10 mm wide at the base and grows to 8 cm long to flowering branches.
- *Number of stems from the crown.*—About 6 main stems, each of these branch at every node.
- *Internode length.*—1 to 4 cm.
- *Surface.*—Pubescent.
- *Color.*—Yellow Green 147D.

Leaf:
- *Type.*—Simple.
- *Shape.*—Olanceolate.
- *Arrangement.*—Alternate.
- *Size.*—Grows to 17.5 cm long and 3.2 cm wide.
- *Margins.*—Entire.
- *Venation.*—Pinnate.
- *Apex.*—Acute.
- *Surface texture.*—Pubescent on both sides.
- *Petiole.*—Grow to 5 mm long and 6 mm wide, pubescent, Yellow Green 145C.
- *Color.*—Top and bottom sides Green 137A with main vein Yellow Green 145C.

Inflorescence:
- *Type.*—Stalked terminal heads, daisy type.

*Peduncle*.—Grows to 19 cm long and 4 mm wide, pubescent, Yellow Green 146C.

*Size*.—Grow to 7.5 cm wide and 3 mm deep.

*Immature*.—2.5 cm deep and 4 cm wide, bowl-shaped with phyllaries and ray florets cupping upwards, ray florets tubular, pubescent, Yellow Orange 21B on the tips with the rest heavily tinted Greyed Purple 185A and veins Greyed Purple 185A, disc 18 mm wide and Greyed Purple 187A on outer half, center Yellow Green 145A.

*Receptacle*.—Disc shaped, becoming 5 mm wide and 1.5 mm deep, Yellow Green 145D.

*Phyllary*.—About 38 in number, cupping upwards; grow to 35 mm long and 7 mm wide, lance-attenuate, margin entire, tip acuminate, pubescent and Green 137A on both sides.

*Disc*.—Conic, deeper with maturity, 27 mm wide and becoming 15 mm deep with maturity, Greyed Purple 187A.

*Lastingness*.—Each inflorescence 7 to 14 days on the plant.

Florets:

*Arrangement*.—Radiate.

*Ray florets*.—Grow to 38 mm long and 29 mm wide, about 30 in number with no pistil or stamen, ovate with the top deeply three lobed; lobes oblong, 15 mm long and 8 mm wide, tip acute, margin entire, glabrous on top and pubescent on the bottom; occasionally with one extra smaller lobe attached on the top side at the top of the limb; topside Greyed Red 179A with the tip Yellow Orange 14A, bottom side Yellow Orange 14A heavily tinted Greyed Red 179A with veins Greyed Red 179A and tip Yellow Orange 14A.

*Disc florets*.—With stamen and pistil, about 170 in number, 18 mm long and 3 mm wide, tubular; corolla 11 mm long and 3 mm wide, 5 lobed, pubescent outside and glabrous inside, Greyed Purple 187A on the top ⅓ to Greyed Red 182C on the bottom ⅔; pistil 1, ovary 4 mm long, hairy, White NN155D, style 7 mm long, White 155A, with extruding 2-branched stigma, Greyed Purple 187A; stamen 5, 7 mm long, Greyed Orange 165C, anthers 5 mm long, pollen Yellow Orange 21A.

*Bloom period*.—June through September in Canby, Oreg.

*Fragrance*.—Light, Chrysanthemum-like.

*Seed*.—None seen.

*Fertility*.—Infertile.

Disease and pests: Insect and disease resistance is believed to be typical for the genus.

I claim:

1. A new and distinct *Gaillardia* plant as herein illustrated and described.

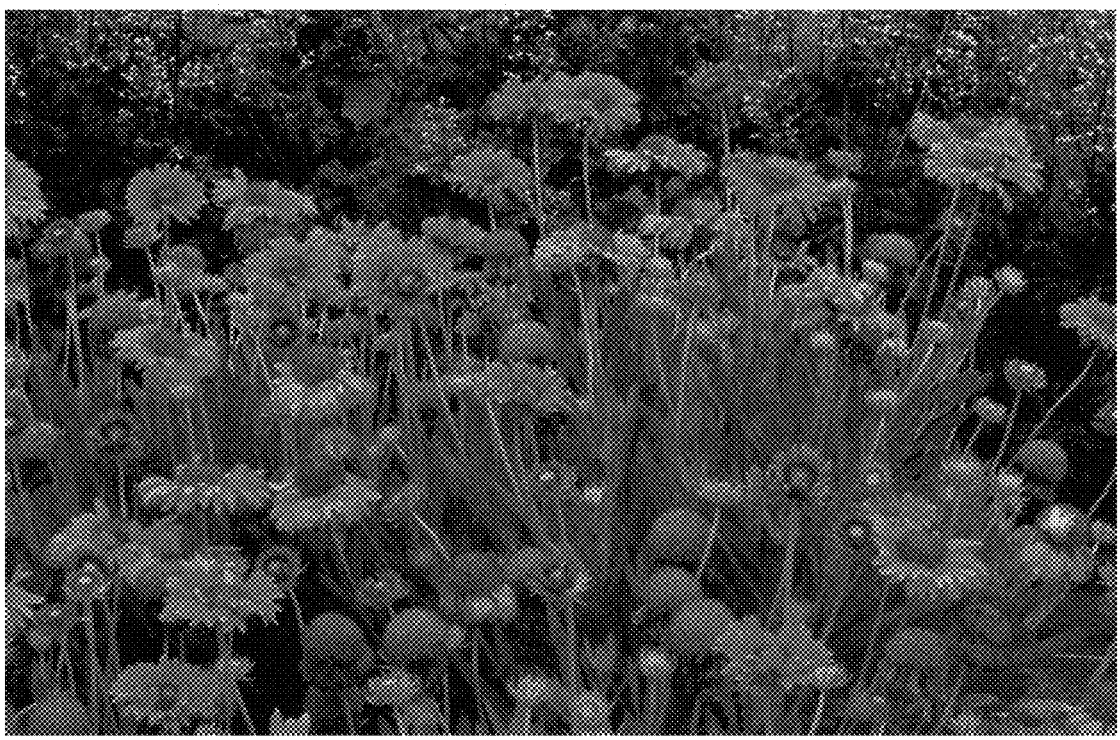

* * * * *